United States Patent
Zylka et al.

(10) Patent No.: US 6,490,477 B1
(45) Date of Patent: *Dec. 3, 2002

(54) IMAGING MODALITY FOR IMAGE GUIDED SURGERY

(75) Inventors: Waldemar Zylka, Hamburg (DE); Roland Proksa, Hamburg (DE); Willem P. Van Der Brug, Eindhoven (NL)

(73) Assignee: Koninklijke Philips Electronics N.V., Eindhoven (NL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/303,317

(22) Filed: Apr. 30, 1999

(30) Foreign Application Priority Data

May 5, 1998 (DE) ............................... 198 19 928

(51) Int. Cl.⁷ ............................................. A61B 5/05
(52) U.S. Cl. ....................... 600/429; 600/417; 600/424; 600/414; 600/426; 606/130
(58) Field of Search ................................ 600/424, 429, 600/407, 414, 417, 426; 606/130; 378/62, 63, 205, 206

(56) References Cited

U.S. PATENT DOCUMENTS 4,998,268 A * 3/1991 Winter
5,872,829 A   2/1999 Wischmann et al. ........ 378/164
6,052,611 A * 4/2000 Yanuf et al.
6,161,033 A * 12/2000 Kuhn

FOREIGN PATENT DOCUMENTS

EP    0600610 A2    11/1993    ........... A61B/19/00

* cited by examiner

Primary Examiner—Marvin M. Lateef
Assistant Examiner—Runa Shah Qaderi
(74) Attorney, Agent, or Firm—John Vodopia

(57) ABSTRACT

An imaging modality, in particular a mobile CT system, comprises an imaging system for imaging an object to be examined. The imaging modality is also provided with an image guided surgery system which includes a position measuring system for measuring positions within the object and a data processor for deriving a transformation between positions within the object and the corresponding positions in the image. The position measuring device is also arranged to measure the position of the imaging system and the data processor is arranged to derive the transformation from the position and/or orientation of the imaging system. The position measuring system is notably an optical position measuring system which is arranged to measure the position of the gantry of the CT system. The data processor is arranged to derive the transformation from the measured position of the gantry. A highly accurate result is obtained when a calibration is carried out which links the position of the CT gantry to the position of the scanning plane.

18 Claims, 6 Drawing Sheets

IMAGING MODALITY FOR IMAGE GUIDED SURGERY

BACKGROUND OF THE INVENTION

1. Field of the Invention

The invention relates to an imaging modality, including an imaging system for forming an image of an object to be examined, and an image guided surgery system, including: a position measuring system for measuring positions within the object, and a data processor for deriving a transformation between positions in the image of the object and corresponding positions within the object. The invention also relates to a method of forming an image of an object to be examined by means of an imaging system wherein a position and/or orientation in the object to be examined is measured. The invention further relates to a method of determining the position of a slice in an imaging system which forms slice images of an examination zone.

2. Description of Related Art

Imaging systems of this kind, capable of forming a slice image of an examination zone for medical purposes, are, for example X-ray computer tomography apparatus, MR apparatus or ultrasound apparatus. Since recently systems of this kind are also used for image guided surgery in order to reproduce or track surgical instruments during an intervention in the body of a patient. The exact position of the surgical instruments can then be determined by means of a position measuring system which measures the position of markers, for example light-emitting diodes (LEDs), provided on the instruments.

An imaging modality of this kind is particularly suitable for use in conjunction with image guided surgery. The image guided surgery system is used to show a position and/or orientation of a surgical instrument in an operating zone within the body of the patient to a user, such as a surgeon, during a surgical intervention. For these applications the object to be examined is a patient to be examined. The patient is examined notably so as to enable a surgical operation to be carried out as well as possible. Such a surgical operation is, for example a (radiological) intervention during which a surgical instrument is introduced into the body of the patient. The surgical instrument introduced into the body of the patient can be used to examine or treat the patient. For the introduction of the surgical instrument use is made of images made before and/or during the operation or intervention, for example X-ray images, computer tomography images or magnetic resonance images. The image guided surgery system includes the position measuring system for measuring the position and/or orientation of the surgical instrument. The image guided surgery system also includes the data processor which is provided with a computer for deriving corresponding positions in a relevant image from the measured positions of the surgical instrument. During the operation the position measuring system measures the position and/or orientation of the surgical instrument relative to the patient and the computer calculates the position and/or orientation corresponding to the measured position and/or orientation of the surgical instrument in such a previously made image. Said previously made image is displayed on a monitor, the actual position and/or orientation of the surgical instrument also being shown therein. The surgeon can observe the image on the monitor so as to see the position of the surgical instrument in the operating zone without having a direct view thereof. For example, the surgeon can observe the image on the monitor so as to determine how to move the surgical instrument in the operating zone without high risk of unnecessary damaging of tissues and notably without risk of damaging vital parts.

An image guided surgery system of this kind is employed, for example in neurosurgery to show the surgeon the exact position of the surgical instrument in the brain during a brain operation.

The imaging modality includes an imaging system. In case the imaging modality is formed by a computer tomography device, the imaging system includes an X-ray source and a detector system. The X-ray source and the detector system are arranged in a number of orientations relative to a patient to be examined in order to acquire a plurality of density profiles. Such density profiles represent the X-ray absorption in the patient to be examined in the respective orientations of the X-ray source and the detector system. One or more images of cross-sections of the patient to be examined are derived from the density profiles. In case the imaging modality is formed by a magnetic resonance device, the imaging system includes receiving coils for receiving magnetic resonance signals. The magnetic resonance signals are generated by spin polarization of nuclei in the patient by means of magnetic fields, followed by excitation of the nuclei. The decay of the nucleus from the excited state is accompanied by the emission of RF magnetic resonance signals. The signal levels of said magnetic resonance signals represent densities of notably protons in the patient to be examined. One or more images of cross-sections of the patient to be examined are derived from the magnetic resonance signals.

An imaging modality used in conjunction with an image guided surgery system is known from European patent application EP 0 600 610.

The known imaging modality includes an ultrasonic position measuring system. Such a position measuring system measures the actual position and/or orientation of a surgical instrument, notably an indicator pen. Furthermore, the patient to be examined is provided with markers which are screwed into the skull of the patient. The imaging modality also reproduces the markers in the image of the patient as formed by the image pick-up system. The position measuring system measures the positions of the markers. The transformation which converts the positions in the co-ordinate system relative to the patient into corresponding positions in the co-ordinate system in the image is derived from the measured positions of the markers and the positions of the images of the markers in the image of the patient. This transformation enables the corresponding position and/or orientation in the image to be derived from the actually measured position and/or orientation of the surgical instrument. The position and/or orientation of the surgical instrument can be reproduced in a rendition of the image of the patient. For example, a rendition of this kind is the image on the monitor showing the image of the patient together with the current position and/or orientation of the surgical instrument.

It is a drawback of the known imaging modality that it is necessary to provide the patient with markers which are screwed into the skull. Providing the markers is a time-consuming operation which is also quite painful to the patient.

SUMMARY OF THE INVENTION

It is an object of the invention to provide an imaging modality which is suitable for use in conjunction with image guided surgery and does not necessitate the use of separate markers in or on the patient.

This object is achieved by means of an imaging modality according to the invention which is characterized in that the position measuring system is also arranged to measure the position and/or orientation of the imaging system, and that the data processor is also arranged to derive the transformation from the measured position and/or orientation of the imaging system.

The location of the region being imaged by the imaging modality is directly linked to the actual position and/or orientation of the imaging system. Furthermore, the image formed by the imaging system is also determined by the adjustment of the imaging system. It has been found that it is possible to derive the transformation between positions in the imaged region and in the image from the position and/or orientation of the imaging system with different adjustments of the imaging system. It is then no longer necessary to use images of separate markers. The adjustment of the imaging system concerns, for example the projection direction and the magnification with which the image is formed. The imaged region contains the part of the object to be examined which is imaged, for example the patient to be examined. The position and/or orientation of the imaging system are measured by means of the position measuring system, for example by picking up images thereof from different directions by means of a camera unit. From the images of the imaging system as picked up by the camera unit, notably from the image signals representing these images of the imaging system, there can be derived the position and/or orientation of the imaging system and hence the region in space which is imaged by the imaging system. From the position of the imaging system of a computer tomography device there can notably be derived the position of the scanning plane at which an image of a cross-section of the patient to be examined is formed by means of the computer tomography device. When the imaging modality is a computer tomography device, the scanning plane is the region in space which is imaged by the imaging system. The transformation which transforms positions in the object into corresponding positions in the image of the object formed by means of the imaging modality can be derived from the measured position and/or orientation of the imaging system and of the object to be examined, notably the patient to be examined or treated. Subsequently, on the basis of this transformation from the measured position and/or orientation of the surgical instrument the corresponding position and/or orientation in the image is calculated. This calculated current position and/or orientation of the surgical instrument is reproduced in the image so that in the image the surgeon can see where exactly the surgical instrument is situated in the patient to be examined and/or treated.

These and other aspects of the invention will be described in detail with reference to the following embodiments.

Preferably, the position measuring system also measures the position and/or orientation of the patient. It is thus achieved that the transformation derived from the measured positions of the patient and of the imaging system accurately takes into account the relative positions of the patient and the imaging system. It is notably possible to take into account motions of the patient, relative to the imaging system and after the images of the patient have been made, in order to derive the transformation.

In a further embodiment of the invention, the object to be examined, for example the patient to be examined, is in a fixed, predetermined position and/or orientation relative to the position measuring system. As a result, it is not necessary to measure the position and/or orientation of the object separately. The position and/or orientation of the patient to be examined relative to the imaging system follows unambiguously from the position and/or orientation of the imaging system measured by means of the position measuring system and the relative positions of the position measuring system and the patient to be examined.

The part of the patient to be imaged thus follows from the measured position and/or orientation of the imaging system and the fixed geometric relationship between the patient to be examined and the position measuring system or the measured position and/or orientation of the patient to be examined; from the relative position and/or orientation of the patient to be examined and the imaging system it can also be derived how said part will be imaged, for example the projection direction and the magnification of the image.

The fixed geometric relationship is preferably established between the patient to be examined and the position pick-up unit of the position measuring system. The position pick-up unit concerns the part of the position measuring system which actually picks up the information as regards the position and/or orientation to be measured. For example, the position pick-up unit is the camera unit whereby images of the imaging system are formed from different directions. The position and/or orientation of the imaging system are derived from these images. The position measuring system measures the position and/or orientation to be measured, for example of the imaging system, relative to the position pick-up unit. Consequently, it suffices when a fixed geometric relationship exists between the patient to be examined and the position pick-up unit, it being irrelevant where other parts of the position measuring system, for example the data processor, are situated relative to the patient to be examined. The data processor, for example, derives the position and/or orientation of the imaging system from signals representing the information picked up by means of the position pick-up unit. The position pick-up unit is preferably mounted on or attached to the object carrier, like a patient table or examination table accommodating the patient to be examined during the examination or the surgical intervention. The fixed geometric relationship between the position pick-up unit and the patient to be examined is thus achieved.

The position and/or orientation of a frame on which the imaging system is mounted can be readily measured. Furthermore, an unambiguous relationship exists between the imaging system and the frame, so that the position and/or orientation of the frame also represents the position and/or orientation of the imaging system. It is notably attractive to provide the frame with one or more radiation sources, such as lamps, LEDs or IREDS. The position and/or orientation of said radiation sources can be very readily picked up by a camera unit, comprising CCD sensors, by picking up images of the radiation sources from different directions. In many cases the frame has enough space for mounting the radiation sources without giving rise to problems. Furthermore, the radiation sources mounted on the frame can be readily observed by the camera unit, because it never or only rarely occurs that the frame, and hence the radiation sources, are shielded from the camera unit. Moreover, it has been found that it is not very important where exactly the camera unit is arranged, because the radiation sources can be observed by the camera unit from most positions.

In a further embodiment of an imaging modality according to the invention, the position pick-up unit, such as the camera unit, is mounted on or attached to the imaging system. For example, the camera unit is mounted on the frame of the imaging system. The position and/or orientation of the imaging system can be determined by picking up the position and/or orientation of a beacon relative to the imaging system by means of the position pick-up unit. This beacon is arranged in a predetermined position and/or orientation within the range of the position pick-up unit. The position pick-up unit then picks up the position and/or orientation of the beacon relative to the imaging system. The beacon also has a predetermined relative position and/or orientation with respect to the object to be examined, for example the patient to be examined or treated, or the relative positions of the beacon and the object to be examined are measured separately. The data processor can readily derive the position and/or orientation of the imaging system with respect to the patient to be examined from the picked up relative position and/or orientation of the beacon and relative positions of the beacon and the object to be examined. For example, the beacon includes one or more radiation sources, such as lamps, LEDs or IREDS, which are arranged in a fixed position and/or orientation at some distance from the imaging system. The position pick-up unit is, for example the camera unit which is sensitive to the radiation emitted by the radiation source. The camera unit is preferably mounted on the imaging system or on the frame of the imaging system in such a manner that the position pick-up unit can suitably pick up the beacon in practically all feasible positions and/or orientations of the imaging system.

In practice the transformation between positions in the image and positions in/on the patient can be particularly accurately derived by calibrating the imaging modality according to the invention. During this calibration, the geometric relationship between the frame, notably the IREDs provided on the housing of the frame, and the region being imaged, such as the scanning plane of the computer tomography device, is accurately derived. A calibration phantom is used for this purpose. The calibration phantom includes imaging elements which can be imaged by means of the imaging system and pick-up elements whose positions can be measured by means of the position measuring system. Furthermore, a fixed geometric relationship exists between pairs of imaging elements and pick-up elements. For example, the imaging elements are X-ray absorbing rods and the pick-up elements are formed by radiation sources such as IREDs or LEDs provided on the X-ray absorbing rods. For example, one IRED is mounted at one end of one of the X-ray absorbing rods. In order to calibrate the imaging modality, an image of the calibration phantom is formed by means of the imaging system, the imaging elements thus being imaged. The region being imaged, notably the scanning plane, can be derived from the positions of the images of the imaging elements. For example, the X-ray absorbing rods converge towards one another and the calibration phantom is positioned in such a manner that the X-ray absorbing rods converge towards one another in a direction transversely of the scanning plane. The situation of the scanning plane can thus be readily derived from the positions of the X-ray absorbing rods and from the spacing of the images of the X-ray absorbing rods in the image of the calibration phantom. Furthermore, the position measuring system measures the positions of the pick-up elements, such as the IREDs at the ends of the X-ray absorbing rods. Because a fixed geometric relationship exists between the former and the pick-up elements, the positions of the imaging elements can be readily derived from the measured positions of the pick-up elements. For example, the positions of the X-ray absorbing rods can be readily derived from the measured positions of the IREDs at the ends of the X-ray absorbing rods. Moreover, the position measuring system measures the position of the imaging system, for example the positions of the IREDs on the housing of the frame. Finally, this calibration determines the relationship between the measured positions of the imaging system, notably the IREDs on the frame, and the region being imaged in the relevant measured position of the imaging system, notably the scanning plane of the computer tomography device. Once the relationship between the measured position and the region being imaged has been calibrated, for the determination of the position of the scanning plane it suffices to measure the position of the imaging system so as to determine the position of the region imaged, for example the scanning plane. The calibration phantom is no longer required after the calibration, so that it is removed from the imaging modality. Preferably, the imaging modality is calibrated anew prior to the beginning of a surgical operation such as a radiological intervention. However, it has been found that accurate and reliable results are also achieved when the imaging modality is calibrated less often, for example once a day or even only once a week.

The method according to the invention is characterized in that a position and/or orientation of the imaging system is measured. Using this method it is not necessary to provide separate markers in or on the patient.

In order to enable planning of such an intervention, but also to enable determination of the position of an instrument during such an intervention, it is necessary to form slice images of the examination zone whose position in space must be accurately known or must be adapted to the position of the instrument.

It is an also object of the present invention to provide a method in which the position of the slice image can be determined in a simple manner. This object is achieved by means of a method of the kind set forth which includes the following steps:

measurement of the position of the imaging system by means of a position measuring system, calculation of the position of the slice from the measured position and from stored calibration data which corresponds to the position of the slice relative to the imaging system.

According to the invention, the position of the slice is not directly measured but only the position of the imaging system (for example, the gantry in the case of a computer tomography apparatus). The position of the slice is calculated from this measured position and from previously determined, stored calibration data which corresponds to the position of the slice relative to the imaging system. When the position of the slice relative to the imaging system is constant and known, for example on the basis of the construction data of the imaging system, the calibration data can be very simply indicated.

Generally speaking, however, the stability of an imaging system is not sufficient to ensure a defined position of the slice relative to the imaging system throughout its service life. Therefore, the calibration data must be repeatedly acquired, for example at intervals of weeks, days or even hours. In a further version of the invention which is suitable for these purposes and which can be used also if the position of the slice relative to the imaging system is even unknown, a calibration phantom is required in which the image elements are configured in such a manner that it is suitably reproduced in the slice image and that its position is defined by the position of the slice relative to the phantom. The calibration phantom is provided with markers which act as the pick-up elements, i.e. the positions of the markers can be measured by the position measuring system. Such a phantom for a computer tomography apparatus is described per se in the U.S. Pat. No. 5,872,829. Analysis of the slice image thus yields the position of the slice in relation to the phantom. The position of the slice relative to the position measuring system or the imaging system can then be calculated by measurement of the position of the phantom and the imaging system.

It would in principle be possible to measure the position of the imaging system or the phantom, for example by means of a video camera system which acts as a position measuring system and derives the position of the imaging system or the phantom from one or more images by automatic image analysis. Position measurement using a phantom with attached markers however, is simpler and also more accurate.

The markers may then be formed, for example by miniature coils which electromagnetically co-operate with the position measuring system or markers which can be detected by means of ultrasound. Preferably, however, in a further embodiment of the invention optically active markers as are used. Instead of the "active" optical markers, use can be made of "passive" markers, for example spherical reflectors which reflect the light originating from an (infrared) illumination system to the optical position measuring system. Passive optical markers of this kind need not be supplied with power.

As has already been mentioned, the need for accurately determining the position of the slice reproduced by a slice image also exists in MR apparatus or in ultrasound apparatus. Particularly advantageous, however, is the application in an X-ray tomography apparatus, which apparatus is also referred to hereinafter as CT scanner. The embodiment is intended for a CT scanner comprising a tiltable gantry includes storage of calibration data for a number of tilt angles, the calibration data for the relevant tilt angle being later used. A further embodiment utilizes the knowledge of the position of the imaged slice in order to guide the imaging system automatically to a given reference position which may be preset, for example, by the position of an instrument provided with markers. The displacement of the gantry relative to the examination zone can then also be performed by displacing the table on which the patient to be examined is accommodated relative to the gantry.

The invention also includes a device whereby the method according to the invention can be performed in an imaging system the device including a position measuring system for measuring the position of the imaging system and means for calculating the position of the slice from the measured position and from stored calibration data, which corresponds to the position of the slice relative to the imaging system. This device enables execution of the method also in the case of imaging systems whose construction data is not known, for example systems manufactured by other manufacturers. The invention also includes the use of such a device in an imaging system.

BRIEF DESCRIPTION OF THE DRAWING

These and other aspects of the invention will be described in more detail with reference to the following embodiments and the accompanying drawing; therein

DETAILED DESCRIPTION OF THE PREFERRED EMBODIMENT

Figure 1:
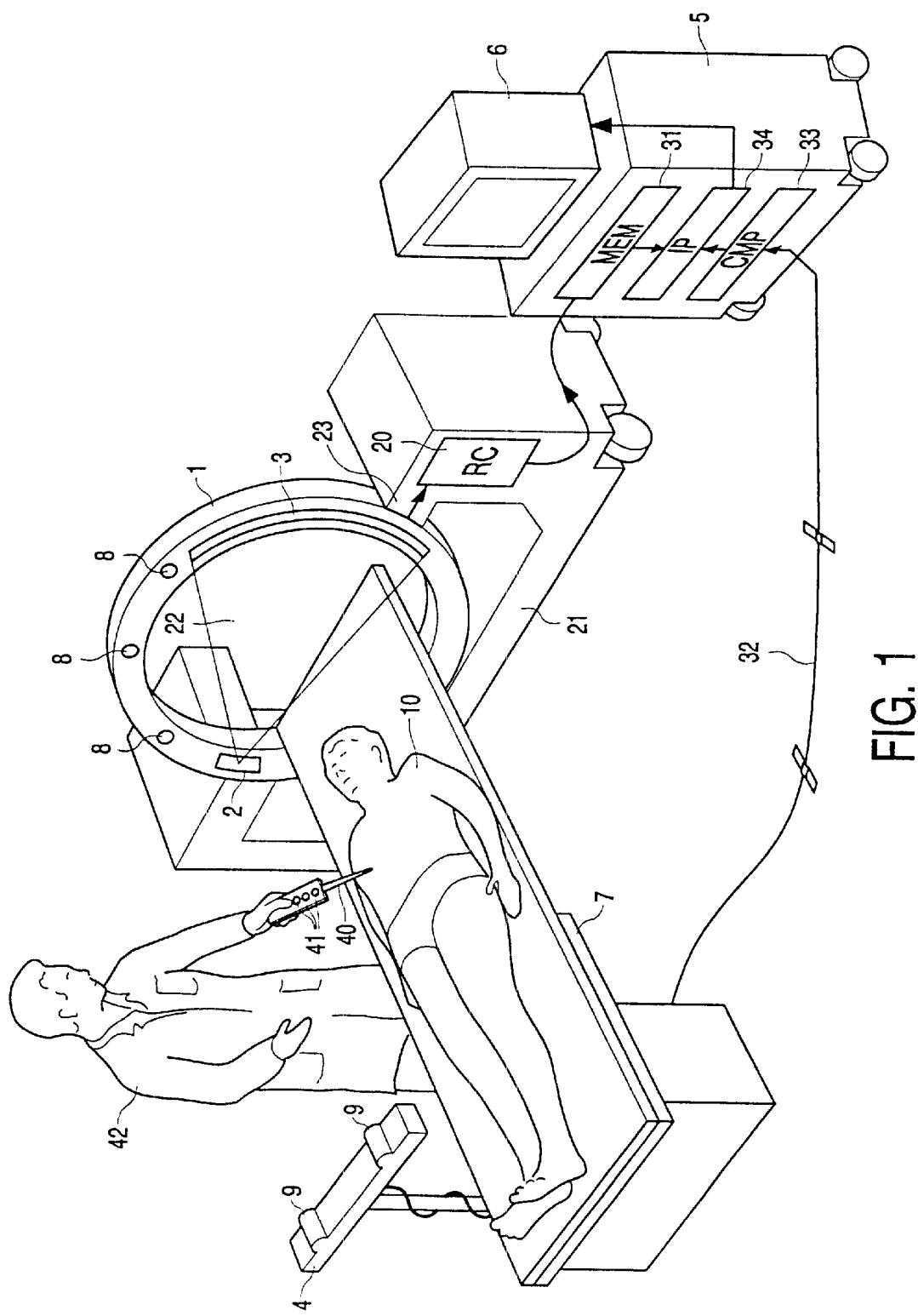
FIG. 1 shows an embodiment of an imaging modality, i.e. a mobile computer tomography system, in which the invention is used.

FIG. 1 shows an embodiment of an imaging modality, i.e. a mobile computed tomography system, in which the invention is used. The computer tomography device includes a frame 1 in which an X-ray source 2 and detector system 3 are suspended. The frame has an annular shape in the present embodiment. The X-ray source 2 and the detector system 3 are rotatable together in the plane of the annular frame 1 and around the patient 10 to be examined. The patient 10 to be examined is accommodated on an examination table 7 which serves as the object carrier. The X-ray source 2 emits an X-ray beam 22 and the detector system 3 picks up density profiles due to local absorption of X-rays within the patient 10. Respective density profiles are picked up for a plurality of directions wherefrom the patient is irradiated by means of the X-ray beam. A reconstruction unit 20 derives one or more images of cross-sections of the patient from the set of density profiles. The reconstruction unit 20 notably calculates the relative densities within the patient 10 by application of (inverse) Radon transformation to the density profiles. The brightness values of the images of the cross-sections are calculated from the relative densities. The images are stored in an image memory 31 which is included in the data processor 5. To this end, the reconstruction unit 20 is coupled to the image memory 31. The computer tomography device is also mounted in a mobile base 21 by way of the frame 1. The frame is tiltable via a hinge system 23, the angle of the plane of the frame 1 relative to the patient 10 thus being adjusted.

The frame 1 is also provided with a number of radiation sources 8, notably infrared emitting diodes (IREDs). Images of the IREDs 8 are picked up from different directions by means of a camera unit 4. To this end, the camera unit 4 is provided with two CCD image sensors 9 which are situated at some distance from one another. It is to be noted that images of the IREDs 8 can also be picked up successively from different directions by means of a single CCD image pick-up device. The camera unit 4 is connected to a computer 33 in the data processor 5 via a cable 32. The image signals, for example electronic video signals representing the images of the IREDS, are applied to the computer 33 via the cable 32. On the basis of the image signals the computer 33 calculates the position and/or orientation of the part of the patient being imaged and the transformation matrix which relates a position and/or orientation within the patient to the corresponding position and/or orientation in the image of the cross-section of the patient. The camera unit 4 and the data processor 5, notably the computer 33, form part of the position measuring system whereby the positions and/or orientations of the imaging system, notably of the frame 1, and of the patient to be examined and of the surgical instrument are measured.

The surgeon or interventionalist 42 examining and/or treating the patient 10 uses a surgical or interventional instrument 40 which is introduced into the body of the patient. The surgical instrument is also provided with IREDs or LEDs 41. The camera unit 4 picks up images of the IREDs 41 on the surgical instrument 40. On the basis of the image signals of the images of the IREDs on the surgical instrument and the previously calculated transformation matrix the computer 33 calculates the corresponding position and/or orientation in the image of the cross-section. An image processing unit 34 derives a processed image signal from the relevant image of the cross-section from the image memory 31 and the calculated corresponding position and/or orientation of the surgical instrument 40 in said image, said processed image signal representing the relevant image of the cross-section together with the current position and/or orientation of the surgical instrument within the patient. The image signal from the image processing unit 34 is applied to the monitor 6 in order to display the image of the patient together with the current position and/or orientation of the surgical instrument 40. The surgeon can observe the monitor so as to see where in the body of the patient the surgical instrument 40 is situated.

Figure 2:
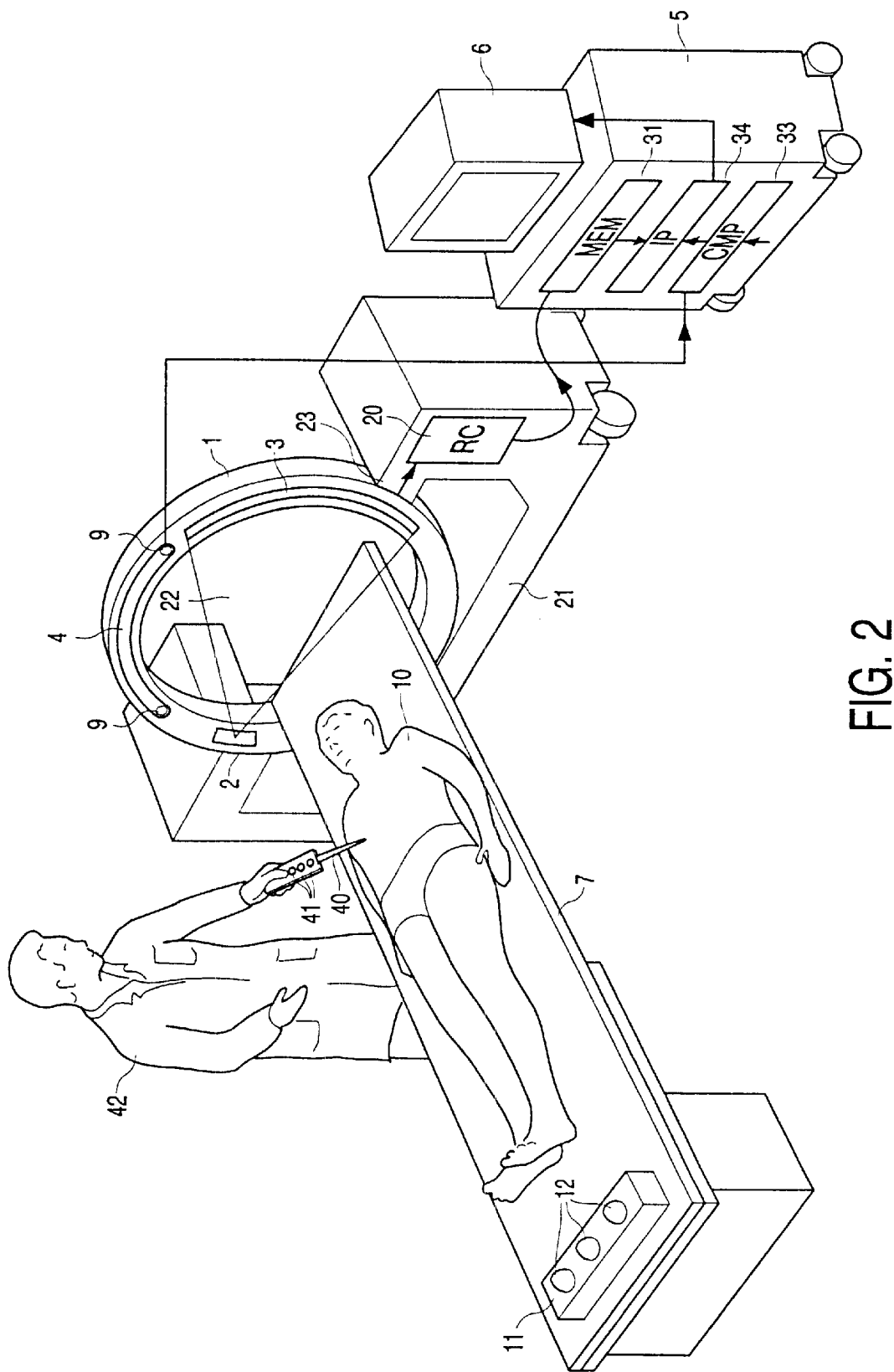
FIG. 2 shows another embodiment of an imaging modality, again a mobile computer tomography system, in which the invention is used.

FIG. 2 shows a further embodiment of an imaging modality, again being a mobile computer tomography system, in which the invention is used. The camera unit 4 with two CCD image sensors 9 is mounted on the frame 1 of the computer tomography device of the embodiment shown in FIG. 2. Furthermore, the beacon 11 is arranged on the object carrier, being the patient table 7. The beacon 11 includes a number of radiation sources 12 which emit radiation whereto the CCD image sensors 9 are sensitive. The radiation sources 12 are preferably IREDs or LEDs wherefrom images are formed from different directions by the infrared sensitive image sensors 9. The camera unit 4 is coupled to the computer 33. The camera unit 4 applies image signals representing the images of the beacon 11 to the computer 33. On the basis of these image signals the computer 33 calculates the position and/or orientation of the imaging system, notably of the frame 1, relative to the beacon 11. The computer 33 derives the transformation, providing the relation between positions in the patient to be examined and the corresponding positions in the image of the patient picked up by the imaging system, from the position and/or orientation of the imaging system relative to the beacon 11 and the position and/or orientation of the patient to be examined relative to the beacon 11. Furthermore, the position measuring system measures the current position and/or orientation of the surgical instrument 40 by picking up images of the IREDs 41 on the surgical instrument 40 from different directions by means of the camera unit 4. The computer 33 calculates the current position and/or orientation of the surgical instrument from the images of the IREDs 41 mounted on the surgical instrument. On the basis of the transformation the corresponding position and/or orientation in the image of the patient is calculated from the current position and/or orientation of the surgical instrument. Furthermore, the image processing unit 34 forms an image signal which represents the image of the patient in which the current position and/or orientation of the surgical instrument is reproduced. This image signal from the image processing unit is applied to the monitor 6 so as to display the image of the patient together with the current position and/or orientation of the surgical instrument within the patient, so that the surgeon 42 can observe the monitor 6 so as to see where in the patient the surgical instrument is situated.

Figure 3:
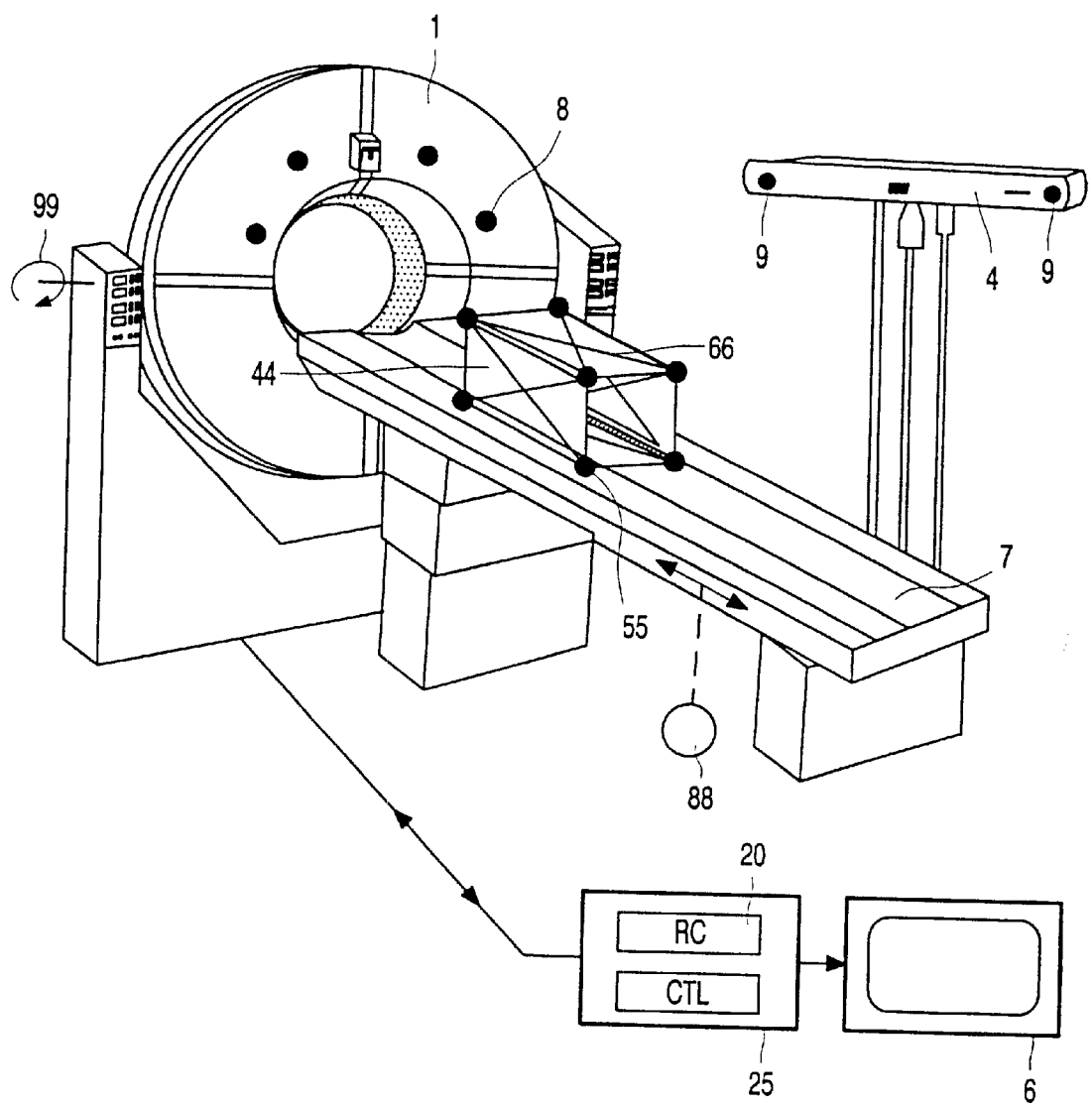
FIG. 3 shows a computer tomography apparatus according to the invention, together with a phantom and a position measuring system.

FIG. 3 shows a CT scanner which includes a gantry 1 and the patient table 7 whose top can be displaced in its longitudinal direction by means of a motor 88. Inside the gantry 1 there are arranged (not shown) an X-ray source which produces a fan-shaped X-ray beam and an X-ray image detector which detects the intensity of the X-ray beam beyond the examination zone. A control 25 and arithmetic reconstruction unit 20 controls the CT scanner and reconstructs one or more slice images from the data supplied by the X-ray detector, the position of said slice images being determined by the path of motion of the X-ray source or the X-ray detector. These slice images can be displayed on the monitor 6. As is denoted by the arrow 99, the gantry 1 can be tilted about a horizontal axis which extends perpendicularly to the longitudinal direction of the table 7, thus enabling the formation of slice images of slices which are situated obliquely in space.

Pick-up elements such as radiation sources that function as markers in the form of light-emitting diodes 8 are attached to the gantry 1. The position of the markers 8, and hence also the position of the gantry, can be measured by means of the optical position measuring system 4 and data processor (5 in FIG. 1) which detects the markers 8 on the gantry 1 by means of the camera unit 4 having two cameras 9 and automatically determines their position, on the basis of their position in the images picked up by the camera systems, in a co-ordinate system $x_s$, $y_s$ and $z_s$ linked to the camera unit 4 of the position measuring system 4 and data processor (5 in FIG. 1).

Figure 6:
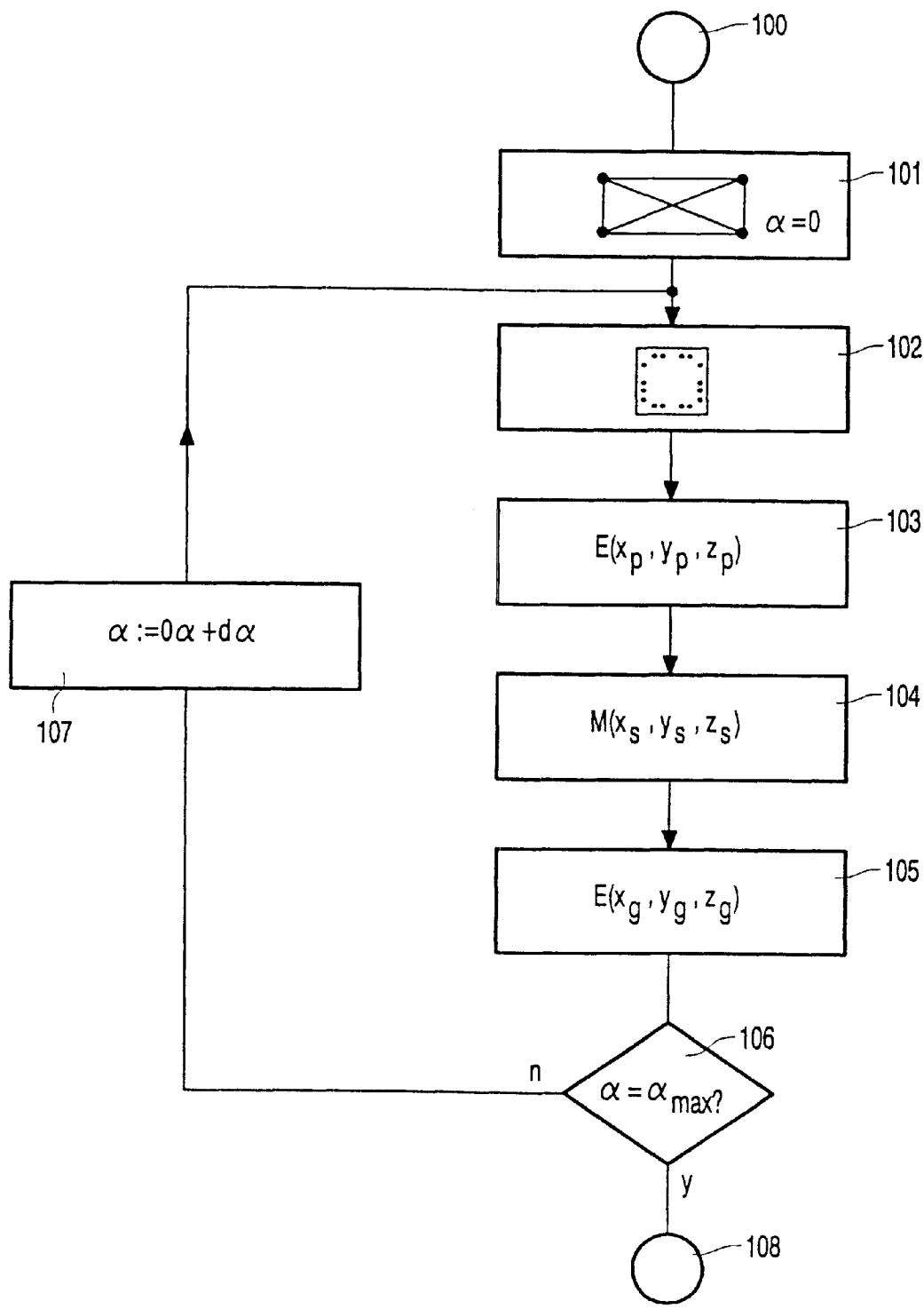
FIG. 6 shows a flow chart illustrating a method of determining the calibration data.

In order to enable exact determination of the position of the slice imaged by means of the CT scanner, first calibration data is determined corresponding to the position of the slice relative to the markers 2 on the gantry. During a later CT examination, the exact position of the reproduced slice in space or relative to the position measuring system can be determined from said calibration data and from the position of the markers 8 on the gantry. The calibration method will now be described in detail with reference to the flow chart shown in FIG. 6.

Subsequent to the initialization 100, a suitable calibration phantom 44 (FIG. 4) is arranged in the gantry 1 in the step 101. This phantom 44 is configured in such a manner that a CT image of a slice of this phantom is unambiguously related to the position of the slice relative to this phantom. The phantom may be, for example a parallelepiped of a synthetic material whose four side faces contain similar, plane structures 66 of bars (for example, of metal) having a high X-ray absorptivity. These bars function as the imaging elements which can be imaged by the imaging system of the CT scanner. These structures may be formed by two X-shaped (but also N, Z or Vshaped) crossing bars whose free ends are interconnected by two bars extending parallel to one another and to the edges of the parallepiped member 44. Markers 55 in the form of light emitting diodes and which act as the pick-up elements, are provided on the phantom, for example at its corners, the position of said markers relative to the structures 66 being accurately defined and known. Therefore, when the position of the markers 55 on the phantom 44 has been measured by means of the position measuring system, the exact position of the structures 66 can be indicated.

The exact positioning of the phantom 44 is not important. It is only essential that the phantom is arranged in the gantry in such a manner that a slice image of the phantom can be formed and that none of the bars of the structures 66 extends perpendicularly to the longitudinal direction of the table 7, because in given circumstances a bar thus situated unless the bar is by chance exactly in the slice plane would not at all be reproduced in a CT image. When the phantom is positioned in this manner, the tilt angle , i.e. the angle enclosed by the gantry relative to a perpendicular plane, equals zero.

Figure 4:
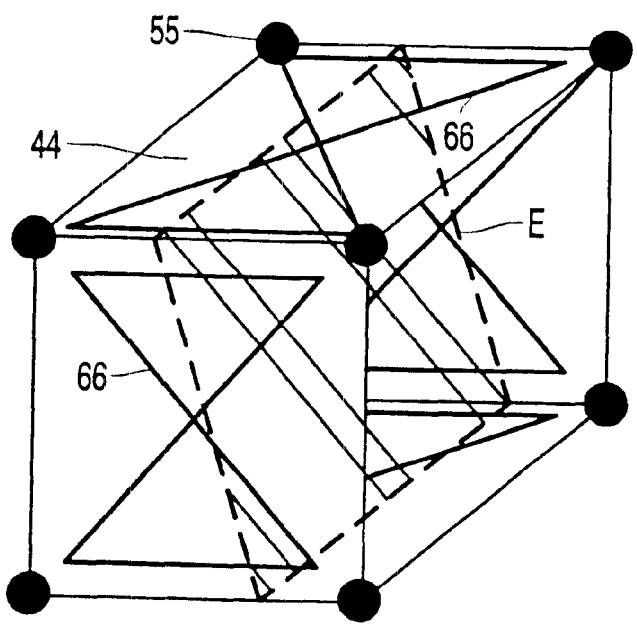
FIG. 4 shows the phantom.

During the step 102 there is formed a CT image which is dependent on the position of the imaged slice in relation to the phantom. This is clearly shown in FIG. 4, showing the phantom and the scanning plane, also denoted as the slice plane reproduced by the CT image and denoted by the letter E. As is shown, each bar of the structures 66 pierces the slice plane in a (piercing) point. The piercing points of one of the structures within one plane are situated on a straight line. Namely, the line which intersects the slice plane E and the plane of the structure 66 at issue. Consequently, in principle the CT image shown in FIG. 5 is obtained, which image generally contains four piercing points for each structure.

Figure 5:
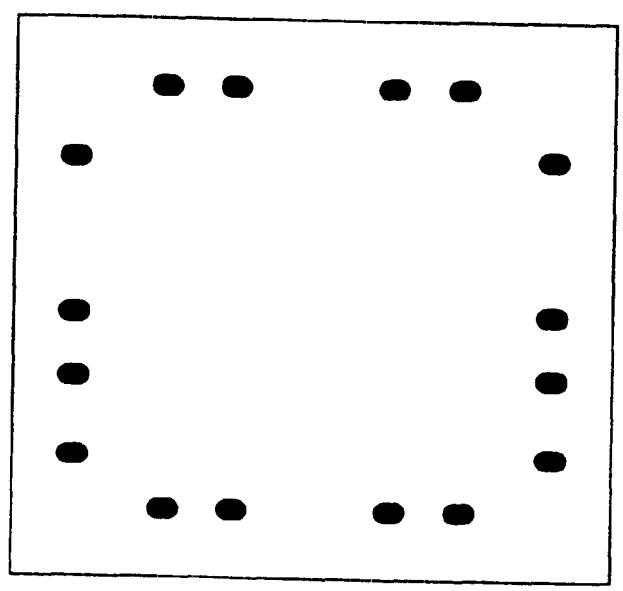
FIG. 5 shows a slice image of such a phantom.

When the line of intersection of the slice plane E with the plane in which one of the structures is situated intersects the outer bars perpendicularly, the inner piercing points are symmetrically situated relative to the outer piercing points on the same line as is shown for the upper and the lower line of points in FIG. 5. However, if the slice plane E intersects the outer bars at an angle other than 90°, the inner piercing points are situated on the same line but asymmetrically relative to the outer piercing points as shown for the left and the right line of points in the CT image of FIG. 5. The closer the two inner piercing points are situated to one another, the smaller the distance from the plane E to the point of intersection of the bars extending obliquely relative to the edges of the phantom will be. When the plane extends exactly through the point of intersection, the two inner piercing points coincide so that the CT image contains only three points on one line.

The foregoing demonstrates that the position of the slice in relation to the phantom can be determined from the CT image. Consequently, in the step 103 the position of all piercing points in the CT image is determined, preferably automatically, by way of an appropriate image processing method. On the basis of these positions in the two-dimensional CT image and the known geometry of the phantom 44 or the structures 66, the position of at least three piercing points defining the plane E is determined three-dimensionally in a coordinate system $x_p$, $y_p$, $z_p$ which is permanently linked to the phantom. During the next step 104, the position of the markers 8 and 55 is measured by means of the position measuring system. This position is thus obtained in a co-ordinate system $x_s$, $y_s$, $z_s$ linked to the position measuring system.

Because the position of the markers 55 on the phantom 44 in a co-ordinate system $x_p$, $y_p$ and $z_p$ linked to the phantom is already known from the start, and because the position of the markers 55 has at the same time been measured by the position measuring system in the co-ordinate system $x_s$, $y_s$, $z_s$ linked thereto, in the step 105 the already determined (in the step 103) position of the slice plane E in the co-ordinate system of the phantom $x_p$, $y_p$, $z_p$ is first calculated in the co-ordinate system $x_s$, $y_s$ and $z_s$ linked to the position measuring system. The slice plane E relative to the gantry is then determined by matching with the previously measured positions of the markers 8 on the gantry, i.e. in a coordinate system $x_g$, $y_g$ and $z_g$ permanently linked to the gantry. These co-ordinates are stored as calibration data in the step 105.

When the gantry again is positioned perpendicularly during a later CT examination, as during this calibration step, the position of the plane E relative to the gantry or relative to the markers on the gantry will then be known. Because the position of the gantry in space or in relation to the position measuring system can be measured thereby, it is then sufficient to measure the position of the markers 2 on the gantry so as to enable determination of the position of the slice plane in space.

During the step 106 it is checked whether the maximum tilt angle of the gantry has already been reached. If this is not the case, the tilt angle a is changed by an increment d and the steps 102 . . . 105 are executed again, the position of the slice plane in relation to the coordinate system $x_g$, $y_g$, $z_g$ linked to the gantry then being stored for this tilt angle. When the maximum tilt angle is after several completions of the loop 102 to 106, the calibration procedure is terminated.

Figure 7:
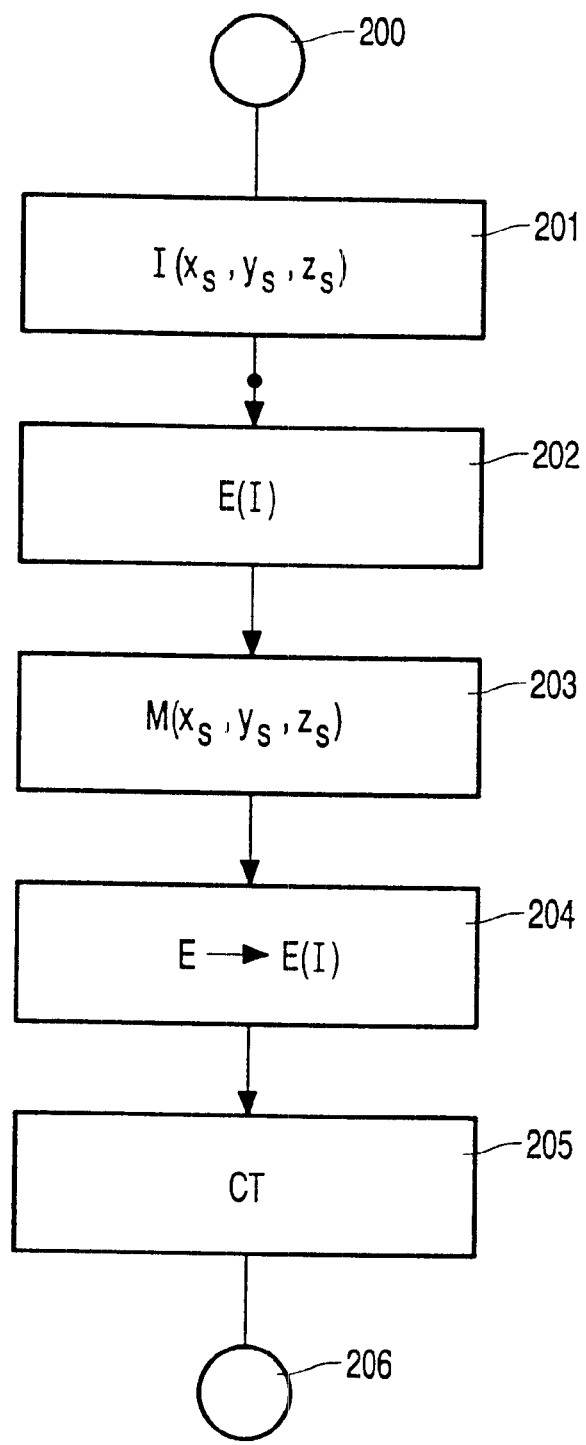
FIG. 7 shows a flow chart illustrating the generating of slice images in a predetermined position.

It is assumed that at a later instant the slice plane of the CT scanner must be moved in such a manner that a surgical instrument introduced into the examination zone is situated exactly in the slice plane. The method required for this purpose necessitates exact knowledge of the position of the slice plane and will be described in detail hereinafter with reference to the flow chart shown in FIG. 7.

After the initialization 200, in the step 201 the position measuring system determines the position of the surgical instrument (not shown) by way of the markers in the form of LEDs which are mounted thereon. On the basis of the position of the instrument determined in the step 201, in the step 202 the position and the orientation of a slice plane which would contain the surgical instrument are determined in a co-ordinate system linked to the position measuring system.

In the step 203 first the position $M(x_s, y_s, z_s)$ of the markers on the gantry is determined (this step could be omitted if it is ensured that the position measuring system and the gantry have not been moved since the calibration). On the basis of the measurement of the position of the markers 200 on the gantry, moreover, in the step 203 the position of the slice plane resulting from the instantaneous position of the gantry is calculated. In the step 204 the gantry can then be tilted and manually or automatically displaced in the longitudinal direction until the slice plane coincides with the plane defined by the instrument. Instead of displacing the gantry, the table top of the patient table can also be displaced by means of the motor 88.

Subsequently, in the step 205 a CT image is formed which completely reproduces the surgical instrument. The procedure is then terminated (206).

It follows from the foregoing that the method according to the invention does not require any knowledge whatsoever concerning the construction parameters of the CT scanner. Using the same requisites (position measuring system, phantom, markers), therefore, the method illustrated with reference to the FIGS. 6 and 7 can also be applied so as to determine the slice plane in a CT scanner from any vendor.

The method according to the invention can be used not only for the formation of single CT slice images, but also for the so-called helical CT method in which the X-ray source and the X-ray detector continuously rotate in the gantry and the gantry and simultaneously the patient table are displaced relative to one another. In that case instead of a single slice a complete volume is reproduced by a series of slices. The position of this volume can be determined by means of a single measurement if additionally the position in time of the measurement within the helical CT examination is measured and if the speed of displacement of the gantry and the patient table relative to one another is known.

Even though the advantages of the method according to the invention become particularly manifest in the case of a CT scanner, the invention is not restricted to such imaging systems. It can also be used for an ultrasound imaging system. The ultrasound transducer therein is also accommodated within a housing, so that the position of the slice plane imaged thereby cannot be exactly indicated. However, if the housing is provided with markers and if the position of the slice plane is measured relative to a phantom which is also provided with markers, the position of the slice plane can subsequently be determined on the basis of the markers on the housing enclosing the ultrasound transducer.

The invention can also be used for MR methods (Magnetic Resonance). Since the position and the orientation of a slice reproduced by an MR image are then also defined by means of magnetic gradient fields, it is difficult to indicate the exact position of the slice plane. This is simply made possible by the method according to the invention. In that case the phantom must be structured in such a manner that the MR contrast of the structure 66 is clearly distinct from the MR contrast of its vicinity.

All references cited herein are incorporated herein by reference in their entirety and for all purposes to the same extent as if each individual publication or patent or patent application was specifically and individually indicated to be incorporated by reference in its entirety for all purposes.

What is claimed is:

1. A system which facilitates image guided surgery on a patient, comprising:
    an imaging system, including a frame located at a position in space, the imaging system for reconstructing a patient image of a patient under examination wherein a fixed geometric relationship exists between the patient and the imaging system,
    a surgical interventional instrument which may be arranged in a position in space that is independent of the position of the frame; and
    an image guided surgery system which may be arranged at a position in space, the image guided surgery system comprising:
    a position measuring system including an position pick-up unit for measuring positions in the patient and a position of the imaging system; and
    a data processor for deriving at least one transformation between the positions in the patient image and corresponding positions within the patient based on the measured position of the imaging system, and at least one transformation between the position of the surgical interventional instrument and the patient image based on the measured position of the imaging system.

2. The system as set forth in claim 1, further comprising an carrier for carrying the patient, and
    wherein the position pick-up unit is mounted on the carrier.

3. The system as set forth in claim 1, further comprising a beacon, wherein said beacon's position is independent of the position of the imaging systems and wherein the position pick-up unit is mounted upon the imaging system frame and arranged to pick up the position of the beacon.

4. The system as set forth in claim 1, wherein the at least one position pick-up unit further includes a camera unit, and
    wherein the imaging system is provided with at least one radiation source to which the camera unit is sensitive.

5. The system as set forth in claim 4, wherein the at least one radiation source is mounted on the frame.

6. The system as set forth in claim 5, wherein the at least one radiation source is one of: a light-emitting diode (LED) and an infrared emitting diode (IRED).

7. The system as set forth in claim 1, wherein the imaging system comprises a computer tomography device.

8. The system as set forth in claim 1, wherein the imaging system comprises a magnetic resonance imaging device.

9. A method of determining the position of a slice of a portion of an examination zone being imaged by an imaging system, the imaging system including a frame fixed in space, comprising:
    measuring a position ($M(x_s, y_s, z_s)$) of the imaging system by means of a position measuring system;
    deriving a transformation between the slice and the measured position of the imaging system from stored calibration data ($E(x_g, y_g, z_g)$) which correspond to the position of the slice relative to the imaging system wherein the calibration data is determined by:
        forming a slice image of a phantom having a known structure,
        determining the position ($E(x_p, y_p, z_p)$) of the slice reproduced by the slice image relative to the phantom,
        measuring the position of the imaging system and the phantom by means of the position measuring system,
        determining the position of the slice relative to one of the position measuring system and the imaging system, and
        storing the calibration data ($E(x_p, y_p, z_p)$) thus acquired, and
    calculating the position of the slice based on said transformation.

10. A method as claimed in claim 9, further comprising utilizing markers which co-operate with the position measuring system and are attached to one of a phantom and the imaging system in order to determine the position of one of a phantom member and the imaging system.

11. A method as claimed in claim 10, wherein said step of utilizing the markers includes that the markers comprise light-emitting diodes and wherein the position measuring system is an optical position measuring system for measuring the position of the markers.

12. A method as claimed in claim 9, wherein the imaging system utilized with said step of measuring comprises utilizing an X-ray computer tomography apparatus which includes a gantry, and wherein the position of the gantry of the X-ray computer tomography apparatus is accomplished by said position measuring system.

13. A method as claimed in claim 12, wherein the gantry can be tilted about an axis, and further comprising the step of:
    determining and storing respective sets of calibration data ($E(x_g, y_g, z_g)$) for a number of tilt angles ($\alpha$), and
    using the set of calibration data ($E(x_g, y_g, z_g)$) determined for the relevant tilt angle ($\alpha$) for a later examination to calculate the position of the slice from the measured positions of the markers on the gantry.

14. A method as claimed in claim 12, wherein said step of measuring includes that one of the gantry and a patient table of the X-ray computer tomography apparatus is displaceable relative to the examination zone, and further comprising a step of forming a slice image in a reference position, by one of automatically displacing the gantry and/or the patient table and by tilting the gantry, until the reference position and the calculated position of the slice correspond.

15. A method as claimed in claim 14, wherein said step of forming includes that the reference position is derived from the position of a surgical interventional instrument introduced into the examination zone and provided with markers.

16. The method of claim 12 wherein the step of utilizing further includes that at least one of the gantry and a patient table of the X-ray computer tomography apparatus is displaceable relative to the examination zone, and further comprises a step of forming a slice image in a reference position by one of automatically displacing at least one of the gantry and the patient table, and by tilting the gantry, until the reference position and the calculated position of the slice correspond.

17. A device comprising:
    an imaging system including a frame for forming slice images of an examination zone,
    a position measuring system for measuring the position of the imaging system, and
    means for determining the position of a slice of a portion of the examination zone being imaged by the imaging system as set forth in the method of claim 9.

18. The device of claim 17 wherein the imaging system comprises an X-ray computer tomography apparatus.

* * * * *